United States Patent [19]

Freedland

[11] Patent Number: 4,721,103
[45] Date of Patent: Jan. 26, 1988

[54] ORTHOPEDIC DEVICE

[76] Inventor: Yosef Freedland, 11871 Artesia Blvd., Artesia, Calif. 90701

[21] Appl. No.: 899,033

[22] Filed: Aug. 18, 1986

Related U.S. Application Data

[63] Continuation-in-part of Ser. No. 696,991, Jan. 31, 1985, Pat. No. 4,632,101.

[51] Int. Cl.⁴ .............................................. A61F 5/04
[52] U.S. Cl. ......................... 128/92 YW; 128/92 YT; 128/92 YY
[58] Field of Search ........ 128/92 YW, 92 YT, 92 YY

[56] References Cited

U.S. PATENT DOCUMENTS

| | | | |
|---|---|---|---|
| 1,269,912 | 6/1918 | Dunham | 128/92 R |
| 4,236,512 | 12/1980 | Aginsky | 128/92 YW |
| 4,409,974 | 10/1983 | Freedland | 128/92 YY |
| 4,519,100 | 5/1985 | Wills et al. | 128/92 YW |
| 4,632,101 | 12/1986 | Freedland | 128/92 YW |

Primary Examiner—C. Fred Rosenbaum
Assistant Examiner—C. W. Shedd
Attorney, Agent, or Firm—Georges A. Maxwell

[57] ABSTRACT

An improved orthopedic implant device comprising an elongate shaft and an elongate sleeve engaged about and shiftable longitudinally of the shaft a plurality of elongate struts spaced circumferentially about the sleeve and shaft and shiftable between unactuated positions where they are parallel with the sleeve and actuated positions where they extend radially outward from the sleeve, pivot means connecting one end of the shafts with the sleeve, lever arms on the shafts projecting into the sleeve from the pivot means therefor and cam means between the lever arms and the shaft whereby the lever arms are pivoted between the unactuated and actuated positions upon axial shifting of the shaft relative to the sleeve.

18 Claims, 28 Drawing Figures

ORTHOPEDIC DEVICE

This is a continuation-in-part of my copending application for U.S. Letters Patent, Ser. No. 696,991, filed Jan. 31, 1985 and which matured into U.S. Pat. No. 4,632,101 on Dec. 30, 1986; for ORTHOPEDIC fastener.

BACKGROUND OF THE INVENTION

The present invention relates to surgical implant devices utilized in procedures where rigid internal fixation of fractured or broken and separated bone portions is desired.

The need for, use and functions performed by and the ends attained by such devices is old and well-known in the art and is clearly set forth in my copending application for U.S. Letter Patent, Ser. No. 696,991, filed Jan. 31, 1985, for ORTHOPEDIC IMPLANT DEVICE, which application is incorporated herein by reference.

I have determined that the implant device which is tne subject matter of and which is illustrated, described and claimed in the above identified copending application has certain structural features and functional characteristics which render it particularly suitable for use in a limited number of situations and which render of questionable utility in other certain situations. Accordingly, I have conceived and invented that improved orthopedic implant device which I will hereinafter describe and claim. My new implant device embodies and puts to use certain structural and functional features of my noted prior implant device and incorporates therewith certain novel improvements which render my improved implant device particularly suitable for use in many of those situations where use of my prior implant device is questionable.

It is to be particularly noted that in the art of orthopedic surgery, physicians exercise great attention and critical care in the selection of those implant devices they will or might use in the practice of their art. In so selecting such devices, the possible shortcomings and/or disadvantages found to exist in substantially all such devices are often afforded greater weight than those advantages that are to be found. As a result, a physician's selection of a particular implant device is, to a great extent, based upon his subjective evaluation of all available devices and a device selected for use is often a compromise device; that is, it is a device which, upon considering and weighing its advantages and disadvantages, meets and/or satisfies that criteria which the physician has set.

In the case of my above noted prior art implant device, certain physicians have expressed their subjective concern regarding the configuration of the pivotally movable struts of that device, which struts, upon implantation and removal of the device, must be forcibly moved through soft, cancellous material of a related bone. The concern expressed is that the noted struts present excessive frontal area and might be difficult to move through and/or might cause excessive displacement of cancellous material. Concern has also been expressed regarding certain structural and mechanical characteristics of my prior implant device which is the subject matter of my application Ser. No. 696,991 now U.S. Pat. No. 4,632,101.

OBJECTS AND FEATURES OF MY INVENTION

It is an object of my invention to provide an improved elongate orthopedic implant device with an inner deployment end portion and an outer securement end portion and a device including an elongate, longitudinally extending central shaft; an elongate outer tubular sleeve about said shaft and shiftable axially relative thereto; a plurality of elongate struts with inner pivot ends and outer free ends; pivot means pivotally securing the pivot ends of the struts to the deployment end portion of the sleeve to allow for pivotal movement of the struts from collapsed unactuated positions parallel with the shaft and sleeve to radially outwardly inclined deployed actuated positions; actuating means at and between the deployment end portion of the shaft and the pivot ends of the struts to pivot the struts upon axial movement of the shaft relative to the sleeve; drive means between the shaft and the sleeve to move the shaft and sleeve axially relative to each other; and anchoring means at the securement end portion of the sleeve to secure the device in working position relative to a related bone structure.

It is an object and feature of my invention to provide a device of the general character referred to wherein the struts elongate, flat, blade-like struts on planes substantially parallel with longitudinal radial planes through the shaft and sleeve and which have radially disposed cutting edges.

Another object and feature of my invention is to provide a device of the general character referred to above wherein the shaft has longitudinally extending recesses to accommodate the struts when the struts are in their collapsed positions and the sleeve has longitudinally extending slots to accommodate and through which the struts move when moved between their unactuated and actuated positions.

Yet another object and feature of my invention is to provide a device of the general character referred to wherein the pivot means for the struts include pivot pins engaged with and between the pivot ends of the struts and the deployment end portion of the sleeve adjacent the slots in which the struts are related.

It is an object and feature of my invention to provide a device of the general character referred to above wherein the struts have lever arms defining cam followers projecting radially inward from their pivot ends and into related recesses in the shaft.

Still another object and feature of my invention is to provide a device of the general character referred to above wherein the actuating means includes cam surfaces in the recesses in the shaft and engaging the cam followers defined by the lever arms on the struts.

Another object and feature of my invention is to provide a device of the general character referred to above wherein the effective length of the lever arms on the struts is greater than the radial extent of the shaft.

Yet another object and feature of my invention is to provide an implant device of the general character referred to above including novel means to disconnect the struts from the sleeve and which includes a wedge tool engageable in the slots in the sleeve and movable relative thereto to yieldingly expand the slotted deployment end portion of the sleeve to disengage the pivot pins that pivotally connect the struts with the sleeve.

The foregoing and other objects and features of my invention will be apparent and will be fully understood from the following detailed description of typical preferred forms and embodiments of my invention, throughout which description reference is made to the accompanying drawings:

DETAILED DESCRIPTION OF THE INVENTION

The preferred embodiment of my improved implant device illustrated in FIGS. 1 through 6 and 8 through 13 of the drawings first includes and is characterized by an elongate central shaft A. The central longitudinal axis of the shaft A is the central axis of the device and, for the purpose of this disclosure, will be described as being vertical. The shaft A has an upper deployment end portion 10 and a lower securement end portion 11.

The shaft A is shown as being cylindrical in cross-section though can be polygonal in cross-section without departing from the spirit of or adversely affecting the invention.

The upper deployment end portion 10 of the shaft is formed with a plurality (2) of elongate, longitudinally extending radially outwardly opening recesses 12. The upper terminal end of the shaft is shown as having an upwardly convergent, conical, pointed end 13.

The recesses 12 in the shaft have flat, laterally spaced opposing sides 14 and radially outwardly disposed bottoms 15. The upper ends of the recesses 12 are formed to define substantially radially extending, substantially downwardly disposed upper cams 16. The lower ends of the recesses have radially extending upwardly disposed bottom ends 17. The upper ends of the recesses are formed with radially inwardly extending outwardly opening cavities 18, below the upper cams 16. The cavities 18 have substantially radially extending, substantially upwardly disposed lower surfaces or edges which converge with the bottoms 15 of the grooves to define lower cams 19, in axial spaced relationship below the upper cams 16.

In practice, the upper portion of the deployment end portion 10 of the shaft A is made polygonal in cross-section to facilitate machining or otherwise establishing the cavities 18 and the vertically spaced cams 16 and 19 and to relieve the upper exterior portions of the shaft adjacent the outer open edges of the recesses and as indicated at 20. Finally, if desired, or found necessary, the shaft A can, as shown, be formed with a longitudinally extending radially outwardly opening keyway 21.

The implant device next includes an elongate tubular outside sleeve B slidably engaged about the shaft A. The sleeve B has an upper deployment end portion 30, a lower securement end portion 31 and a plurality (2) of an elongate, longitudinally extending radially opening slots 32 with opposing parallel sides 33 and bottoms 34. In practice, the upper ends of the slots can, as shown, be open.

The slots are coextensive with and are in register with related recesses 12 in the shaft A.

The upper portion of the upper deployment end portion of the sleeve B occurs about the upper polygonal portion of the shaft A and is provided with axially spaced axially aligned pin receiving openings 35 on cord lines through the sleeve and the relieved portions of the shaft A. The cord lines or axes of the openings 35 are spaced radially outward of and are normal to the longitudinal axis of the device.

Figures 1, 2, 3, 4, 5, 6, 7, 21, 22:
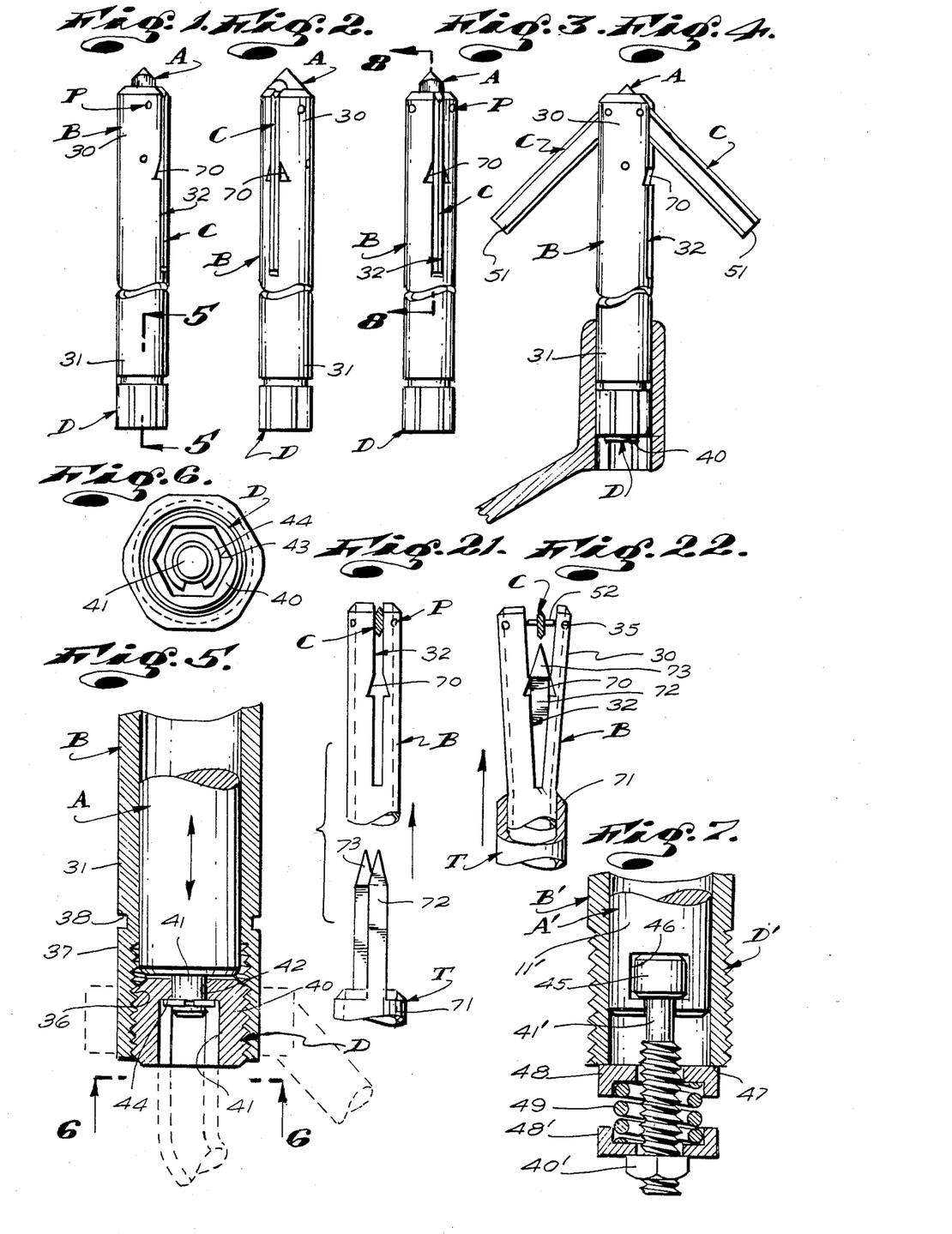
FIG. 1 is an elevational view showing one side of my improved implant device in an unactuated position.
FIG. 2 is a view similar to FIG. 1 showing the device rotated 45°.
FIG. 3 is a view similar to FIG. 1 showing the device rotated 90°.
FIG. 4 is a view similar to FIG. 1 showing the device in an actuated position and related to a mounting fixture.
FIG. 5 is an enlarged detailed sectional view taken substantially as indicated by line 5—5 on FIG. 1.
FIG. 6 is a view taken substantially as indicated by line 6—6 on FIG. 5.
FIG. 7 is a view similar to FIG. 5 and shows another embodiment of the invention.
FIG. 21 is an exploded view showing portions of my device and a related releasing tool.
FIG. 22 is a view showing a portion of the device and the releasing tool engaged.

In the form of the invention now under consideration, the lower securement end portion 31 of the sleeve B is internally threaded, as at 36 in FIG. 5 of the drawings. The lower portion 31 of the sleeve is provided with circumferentially spaced radially outwardly disposed tool engaging flats 37 and with an annular radially outwardly opening tool engaging and/or retaining pin receiving channel 38. The flats 37 are provided to facilitate engaging the sleeve with a wrench, as shown in dotted lines in FIG. 5, to hold the sleeve against rotation if such is required. The groove 38 is provided to receive a tool or tool part (not shown) to facilitate moving and/or setting the sleeve in set axial position when the device is installed and/or removed from engagement in a related bone structure.

In practice, the securement ends of implant devices of the character here concerned with are cooperatively related to a number of different kinds of mounting hardware and must often be especially formed to facilitate their being related to certain selected kinds of hardware. For example, and as shown in FIG. 7 of the drawings, the lower end of the sleeve B' can be externally threaded, as at 39, to facilitate its being threadedly engaged with some particular form of mounting hardware or special tool part. In accordance with the foregoing, it is to be understood and will be apparent that the lower securement end portion of the sleeve of my implant device can be especially formed to be related to various different tools and mounting hardware without departing from the spirit of or adversely affecting the novelty of my invention.

The implant device next includes drive means D to move the shaft A from an upper unactuated position within the sleeve B to a lower actuated position within the sleeve and to return the sleeve from said actuated to said unactuated position, as desired and as circumstances require.

The drive means D, shown in FIG. 5 of the drawings, includes a threaded drive part 40, accessible at and drivingly connected with and between the lower securement end portion of the shaft A and the lower securement end portion of the sleeve B. The drive part 40 is engageable with a manually operable hand tool. When rotated, the part 40 functions to move the shaft axially relative to the sleeve.

In the form of the invention now under consideration, the drive part 40 of the means D is an Allen screw-type part, threadedly engaged in the internal threaded portion of the sleeve. The screw part 40 is drivingly coupled with the lower end of the shaft for free relative rotation and against axial movement by a central vertical coupling pin 41 depending from the shaft and into and through a central opening 42 in the part 40. The pin 41 terminates in the upper end portion of the downwardly opening tool receiving socket 43 in the part. The pin 41 has a snap ring receiving groove in its lower end portion in which groove a snap ring or radially outwardly extending retaining part 44 is engaged. The snap ring or part 44 opposes and establishes sliding engagement with the downwardly disposed bottom of the socket 43, whereby axial driving engagement is established between the part 40 and the shaft.

In FIG. 7 of the drawings, I have shown an alternative form of drive means D'. The drive means D' includes a threaded drive part 40', which part is in the form of an ordinary or common nut. The part 40' is coupled to the shaft A' for free rotation by a central vertically extending coupling pin 41' depending from the shaft and threadedly engaged in and through the part 40'. The coupling pin 41' has an enlarged head 45 at its upper end, which head is engaged in a transversely extending T-slot 46 formed in the lower end portion of the shaft, as clearly illustrated.

The drive part 40' of the means D' is drivingly connected with the downwardly disposed annular bottom end 47 of the sleeve B' by upper and lower washer like spring seat parts 48 and 48' and an intermediate coil compression spring 49 engaged about the pin 41' and between the end 47 of the sleeve and the part 40'.

The drive means D' illustrated and described above allows for spring biasing of the device for limited relative axial shifting of the shaft and sleeve, when the device is in use. Such spring loading of the device is desirable in certain circumstances where limited resilient movement of parts of the device is sought to be provided for.

The implant device A next includes a plurality (two) of elongate blade-like struts C with inner pivot ends 50 and outer free ends 51. The struts C are slightly less in longitudinal extent than the longitudinal extent of the slots 31 in the sleeve B and the recesses 12 in the shaft A. The struts C are engaged in said slots and recesses for pivotal movement from unactuated or collapsed position where they are substantially parallel with the longitudinal axis of the device and extend longitudinally within said slots and recesses, to actuated or deployed positions where their axes are angularly related to said central axis of the device and where they extend radially and axially outward from within said slots and recesses and from the exterior of the sleeve.

The flat blade-like struts C have flat central longitudinal planes which are parallel with the central longitudinal planes of their related recesses and grooves 12 and 32 and are slidably engaged in said recesses and grooves for lateral support and for free pivotal movement. The struts have substantially radially inwardly and outwardly disposed opposite inner and outer side edges 52 and 52' which are preferably sharp cutting edges. The sharp cutting edges 52 and 52' allow for pivotal movement of the struts through cancellous bone material with the application of minimum force and with minimum disturbance to that material, when the struts are moved between their actuated and unactuated positions.

The upper pivot ends 50 of the struts carry elongate laterally extending pivot pins 53. The pivot pins 53 are preferably press-fitted in openings in the struts on axes normal to the central radial planes of the struts. The pins project laterally from opposite sides of the struts. The opposite free end portions of the pins are slidably engaged in those pairs of aligned openings 35 in the sleeve related to each of said slots and pivotally connect the struts to the sleeve, as clearly shown in the drawings.

The openings 35 and the pivot pins 52 cooperate and establish pivot means P for the several struts and the turning axes for said struts.

In the case illustrated, the central portions of the pins 52, engaged through the struts and projecting from the opposite sides thereof, extend across cord lines within the sleeve B and are slidably accommodated by the relieved portions of the shaft, as clearly shown in FIGS. 8 through 13 of the drawings. The relieved portions 20 of the shaft eliminate interference between the pins and the shaft and assure free axial movement of the shaft within the sleeve.

The struts C next include elongate lever arms 60. The lever arms are preferably formed integrally with and project upwardly and radially inward from the pivot ends of the struts and their related pivot pins 52. The lever arms 60 are shown defined by simple extensions of the struts and are formed to establish a cam follower 61 that establishes sliding driving engagement with and between the upper and lower cams 16 and 19, defined in the shaft by the upper ends of the recesses 14 and the cavities 28 in the shaft.

In the form of my invention now under consideration, the lever arms have inside cam follower edges parallel with and extending longitudinally from the inner edges 52' of the struts and have longitudinally outwardly and radially inwardly extending outer cam follower or stop edges angularly related to and which converge with said inner cam follower edges to define a cam follower point. The cam follower point is preferably radiused, as clearly illustrated in the drawings.

The cam followers 61 and their related cam surfaces 16 and 19 cooperate to establish cam acuating means M to pivot the struts C about their turning axes defined by the pivot pins 52, upon axial movement of the shaft A relative to the sleeve B.

Figures 8, 9, 10, 11, 12, 13, 14:
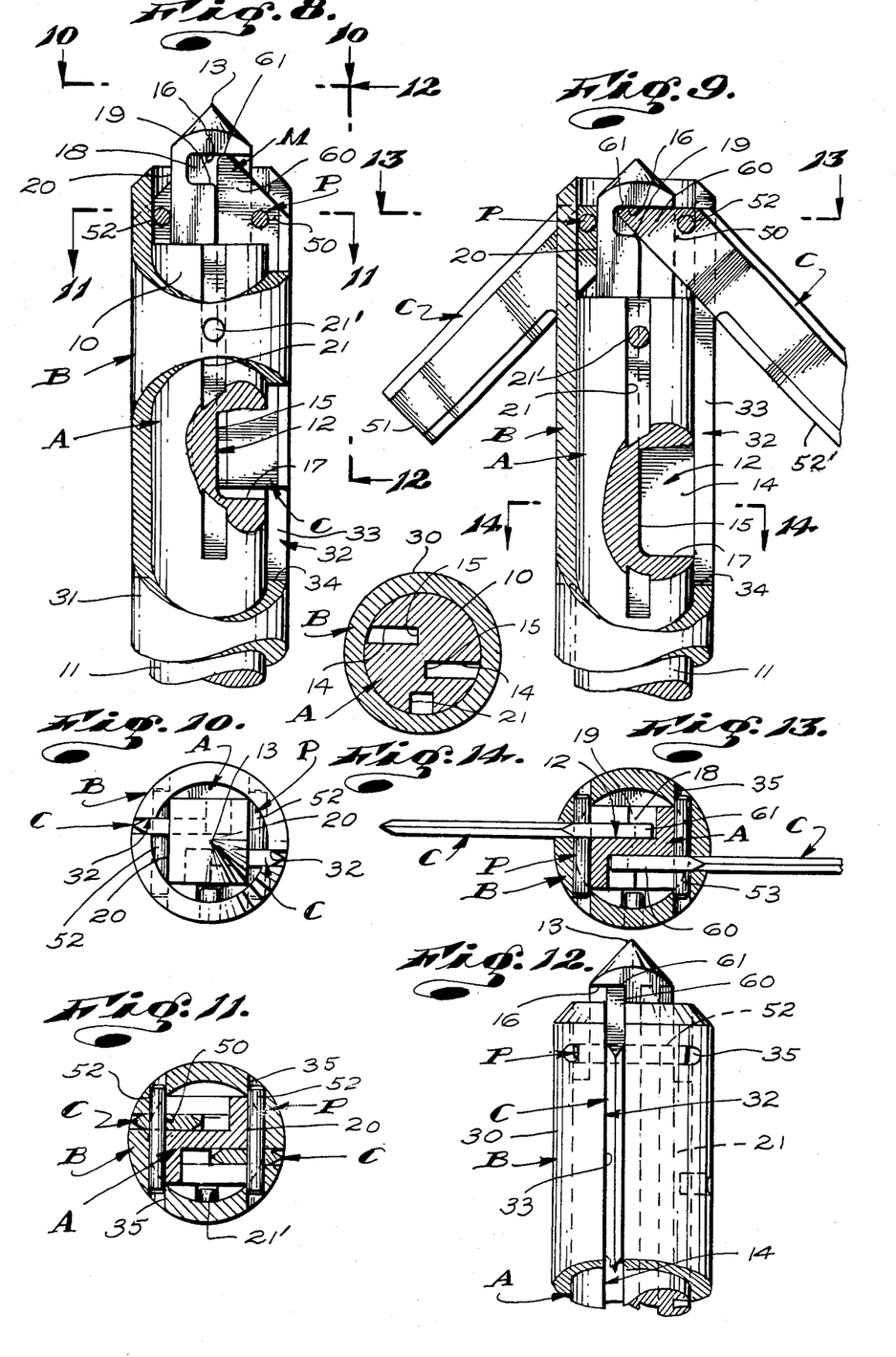
FIG. 8 is an enlarged detailed sectinal view taken substantially as indicated by line 8—8 on FIG. 3.
FIG. 9 is a view similar to FIG. 8 showing the structure in another position.
FIG. 10 is a view taken substantially as indicated by line 10—10 on FIG. 8.
FIG. 11 is a sectional view taken substantially as indicated by line 11—11 on FIG. 8.
FIG. 12 is a view taken substantially as indicated by line 12—12 on FIG. 8.
FIG. 13 is a view taken substantially as indicated by line 13—13 on FIG. 9.
FIG. 14 is a view taken substantially as indicated by line 14—14 on FIG. 9.

As shown in FIG. 8 of the drawings, when the device is in its unactuated position, with the shaft A in an up position relative to the shaft sleeve, the struts C are in collapsed position within their related slots and recesses and the points of the cam followers 61, which occur radially inward of and above the pivot pins 52, engage the top cam surface 16. When the shaft A is moved down within the sleeve from its unactuated position to an actuated position, by operation of the drive means D, the upper cam surface 16 moves down and pivot the lever arms downwardly and inwardly and the struts upwardly and outwardly from their collapsed or unactuated positions. As the lever arms pivot inwardly and downwardly, they swing into the confines of the cavities 18 and the lower cams 19, defined by the cavities 18 and the bottoms 15 of the recesses, establish sliding bearing engagement with the inner cam follower edge of the cam follower 61, as clearly shown in FIG. 9 of the drawings.

In the preferred carrying out of my invention, the lever arms 60 and cam followers 61, defined by said arms, are preferably formed so that when the struts are fully actuated and deployed, the outer cam follower edges establish parallel stopped engagement with the upper cam surface 16 and the cam points of the cam follower stop against the bottoms of the cavities to provide strong and sound support for the struts.

In practice, the portions of the outer cam follower edges that extend radially outward from the cam follower points are and might better be defined as stop edges since while they move into and out of stopped engagement with the cam surfaces 16, they do not establish continuous bearing engagement with and/or follow those cam surfaces.

When it is desired to pivot and move the struts from their deployed or actuated positions to their collapsed or unactuated positions, the shaft A is moved up within the sleeve B by the drive means D and the lower cams 19 act upon the inner cam follower edges of the cam followers 61 and pivot the lever arms upwardly and radially outward and the struts radially inwardly and downwardly until they are returned to their unactuated or collapsed positions.

It is to be noted that when the struts C are in their unactuated or collapsed positions within the slots 23 and recesses 12, they are suitably protected and are retained against lateral displacement. Further, when the struts are in their actuated or deployed positions, sufficient portions of the pivot end portions of the struts and their related lever arms remain engaged in the slots and recesses to afford substantial and adequate lateral support for the struts and prevent lateral displacement thereof. The foregoing support for the struts is augmented or supplemented by the pivot pins 53 which are in sliding supported engagement with the flat relief surfaces 20 on the shaft.

In the preferred carrying out of my invention and as best shown in FIGS. 11 and 14 of the drawings, the two recesses 12 in the shaft are in lateral spaced relationship from each other and occur in radial spaced relationship at opposite sides of the central axis of the shaft. With such a special and unique relationship of the recesses, the recesses and their related cavities 18 are non-interfering and can be made substantially greater in depth than if they were on a common radial plane through the shaft. By this novel relationship of the recesses and cavities, the dimensions of the struts C between their edges 52 and 52' can be made notably greater so as to impart the struts with greater strength, without adversely affecting the ability of the device to be implanted or removed from implantation within a bone structure. More important, the effective length of the lever arms can be made notably greater to impart the cam means with greater mechanical advantage.

Since the use to which my implant device is intended to be put and the manner in which it might be implanted in related to bone structures to be worked upon is well-known in the art and is fully described in my above identified copending application, illustration and detailed description of the use to which it is put can be and will be dispensed with.

When the struts are in their fully acutated or deployed positions, they are preferably set and supportingly stopped at an angle of 45° relative to the central axis of the device.

In practice, the longitudinal extent of the struts C is sufficiently great so that the outer free end portions thereof can be cut and formed to establish proper and desired engagement with related opposing surfaces in a related bone structure. The proper length of the struts and the proper shape of the free ends thereof, for any particular implantation, can be determined by the utilization and studying of X-rays of the bone structure to be worked upon.

In practice, there are certain known situations where it would be necessary that the struts, when actuated, be pivoted radially outwardly and downwardly relative to the shaft and sleeve so that when deployed they extend radially outwardly and upwardly relative to the shaft and sleeve.

Figures 15, 16, 17:
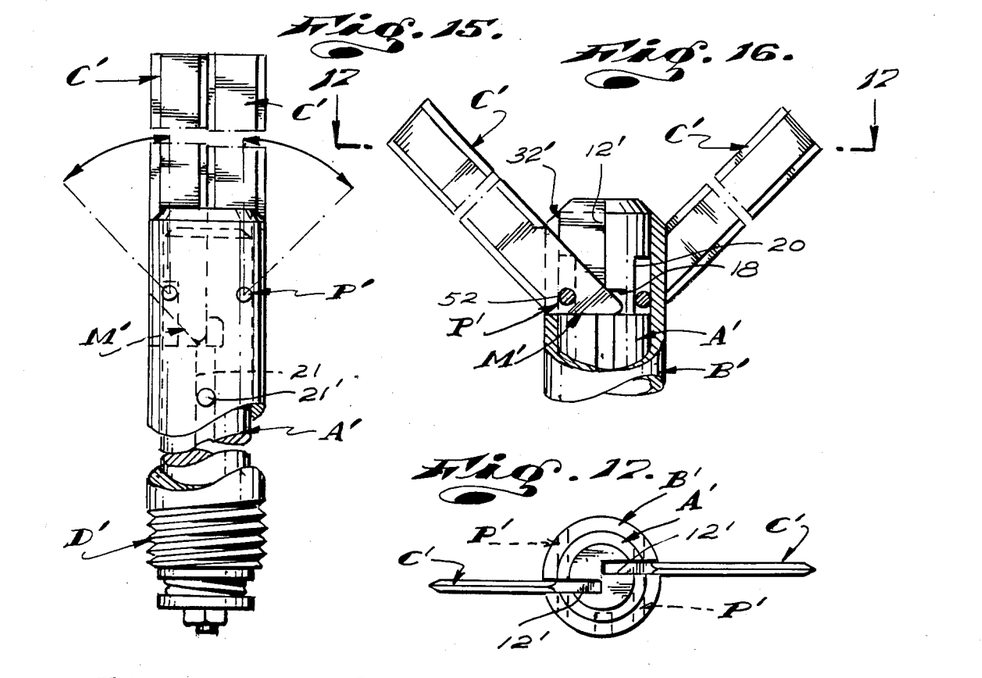
FIG. 15 is a longitudinal elevational view illustrating another embodiment of my invention.
FIG. 16 is a sectional view of a portion of the structure shown in FIG. 15 with parts in another position.
FIG. 17 is a view taken substantially as indicated by line 17—17 on FIG. 16.

In accordance with the above and as shown in FIGS. 15, 16 and 17 of the drawings, the cam means M' at the upper deployment end portion of the shaft A' is reversed or turned upside down. Further, the recesses 12' are reversed to extend longitudinally upward and open axially at the upper terminal end of the shaft. The radially and axially upwardly opening slots 32' in the sleeve B' can be and are shown substantially shorter than they are in the first embodiment of my invention. The struts C' are turned over or reversed to extend axially upward from the pivot means P' and project axially upward from the upper ends of the shaft and sleeve when in their unactuated or collapsed positions. When the struts are in their actuated or deployed positions, they project radially outwardly and upwardly relative to the central axis of the device. In all other respects, the modified embodiment of my invention now under consideration is similar to my first embodiment of the invention and like parts, portions and means are identified by like reference characters, where appropriate.

In the above noted second embodiment of my invention, the device operates in the same manner as in the first embodiment of my invention except that, as a result of the rearrangement and reversal of certain of the parts and portions thereof, the struts extend radially outward and upward relative to the central axis of the device, when deployed.

Figures 18, 19, 20:
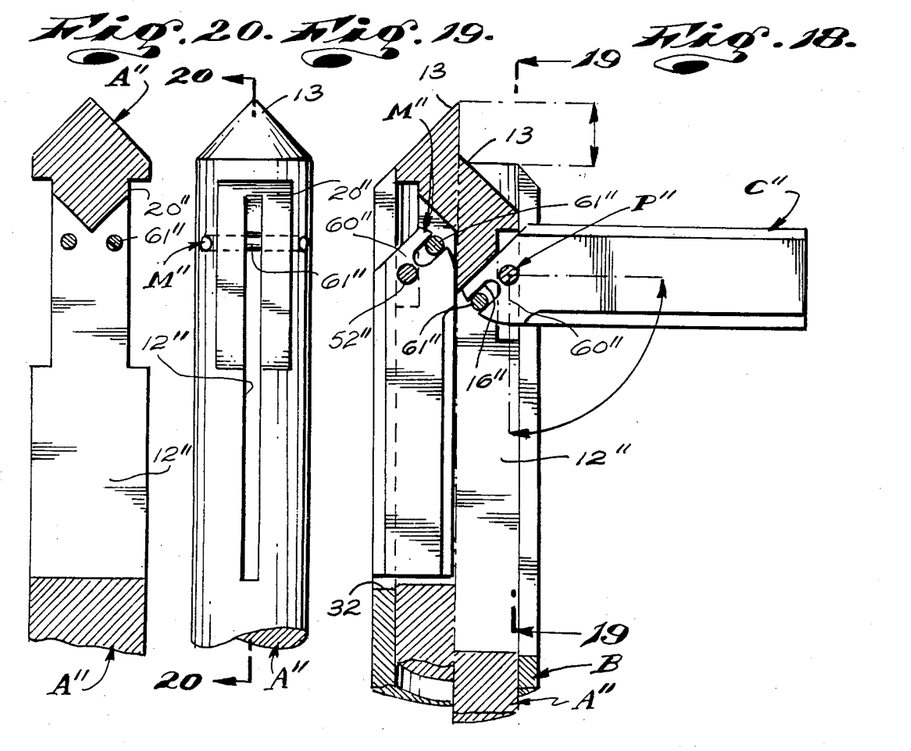
FIG. 18 is a split longitudinal sectional view of another embodiment of my invention showing parts in unactuated and actuated positions.
FIG. 19 is an elevational view of the shaft in FIG. 18 and taken substantially as indicated by line 19—19 on FIG. 18.
FIG. 20 is a sectional view taken substantially as indicated by line 20—20 on FIG. 19.

In FIGS. 19, 20 and 21 I have illustrated a third embodiment of my invention wherein another and different form of cam means M' is provided between the shaft A" and the lever arms 60" on the struts C" to pivot said struts between their unactuated and actuated positions, upon relative axial shifting of the shaft and sleeve by operation of the drive means (not shown). The cam means M" includes spaced pairs of cam surfaces 16" and 19" established by elongate cam slots in the lever arms 60". The cam slots and the cam surfaces 16" and 19" extend radially relative to their related pivot pins 52' of the pivot means P". The cam means M" next includes cam followers 60" engaged with the cam surfaces 16" and 19". The cam followers 61" are elongate cam pins carried by the shaft on axes normal to their related lever arms and are slidably drivingly engaged in the cam slots and with the cam surfaces 16" and 19".

Referring to FIG. 18 of the drawings, which is a longitudinally split cross-sectional view of the third embodiment of my invention wherein one-half of the structure is shown in an unactuated position and the other half is shown in an actuated position, it will be apparent that upon axial shifting of the shaft relative to the sleeve, the struts can be selectively moved between their unactuated and actuated positions, as desired.

In this third embodiment of my invention, the recesses 12" are on a common plane and communicate with each other. Thus, as shown in FIGS. 19 and 20 of the drawings, the shaft A" is a simple part that can be easily and economically made.

In the third embodiment of my invention, the struts C" can be pivoted a full 90° and when fully actuated, extend radially outward from the sleeve and shaft.

In all other respects, this third embodiment of my invention can be substantially the same as my first embodiment of the invention and in the drawings, like and/or corresponding parts have been identified with the same reference characters, where appropriate.

In practice, it is possible that after the implant device that I provide has been implanted in a bone structure, with the struts deployed, bone material will grow about the device in such a manner that the struts cannot be effectively and/or safely moved from their actuated to their unactuated positions by operation of the drive means D, preparatory to removing the implant device. In such situations, it is necessary that the struts be disconnected from the sleeve to allow for easy and safe removal or extraction of the shaft and sleeve assembly from their related bone structure. Upon removal or extraction of the shaft and sleeve assembly, the struts, left to remain in the bone structure, can be safely removed, one at a time.

In accordance with the above and to disconnect the struts from the sleeve, I form the sleeve with access openings 70 with upwardly convergent edges. The access openings 70 are preferably located intermediate the upper and lower ends of the slots and in spaced relationship below the pivot pins 53 of the pivot means P. The access openings 70 are positioned to be intersected by their related slots with their upwardly convergent edges intersecting related sides of the slots, as clearly shown in FIG. 21 of the drawings.

Next I provide an elongate releasing tool T with a lower tubular body 71 that is slidably engageable about the lower securement end portion of the sleeve and can be manually moved upwardly relative thereto. The tool T has a pair of elongate resilient arms 72 projecting axially upward from the body 71 in alignment with and overlying the exterior of the slots 32. The upper ends of the arms 72 have radially inwardly projecting upwardly tapered wedges 73 which engage the exterior of the sleeve and bias the arms outwardly when the tool is initially engaged about the sleeve and is advanced upwardly relative thereto. When the wedges 73 reach the access openings 70, they are yieldingly moved into cooperative engagement therein by the arms. Upon subsequent upward movement of the tool T, the wedges 73 are advanced up from the opening 70 into the slots and yieldingly bias and spread apart the portions of the sleeve defining the slots. Such biasing of the sleeve moves the upper portions thereof in which the pivot pins of the means P are engaged out of engagement with said pivot pins to effectively disconnect the struts from the sleeve, as clearly shown in FIG. 22 of the drawings.

Figures 23, 24, 25, 26:
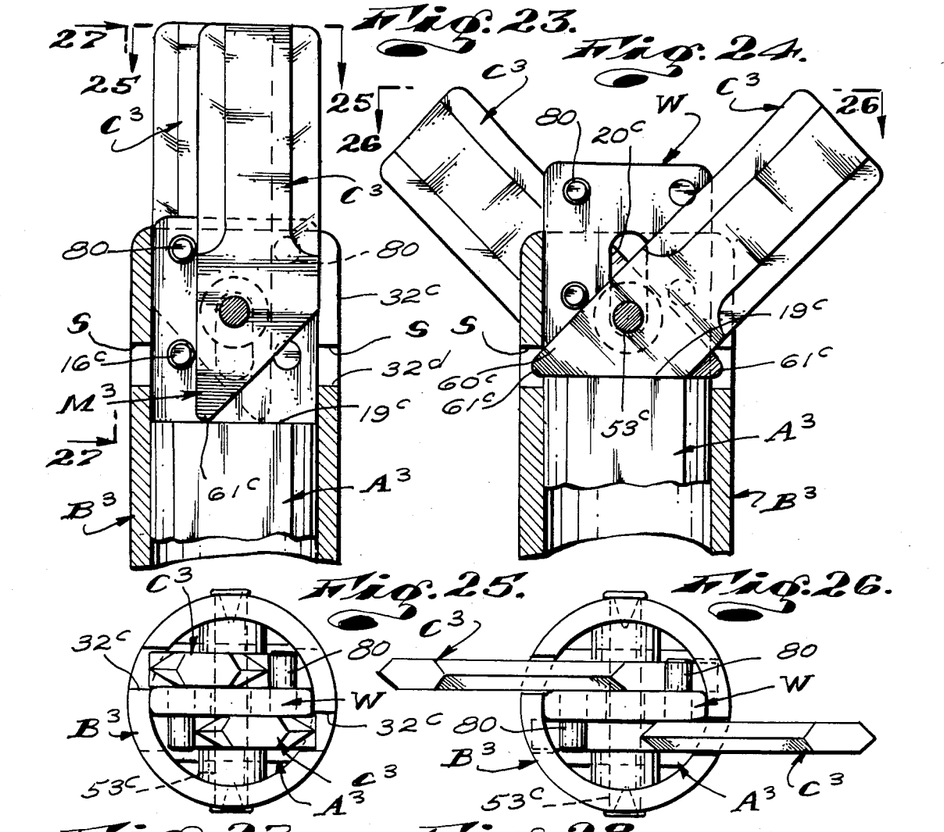
FIGS. 23 and 24 are similar to FIGS. 15 and 16 and show another embodiment of my invention.
FIG. 25 is a view taken on line 25—25 on FIG. 23.
FIG. 26 is a view taken on line 26—26 on FIG. 24.
Figures 27, 28:
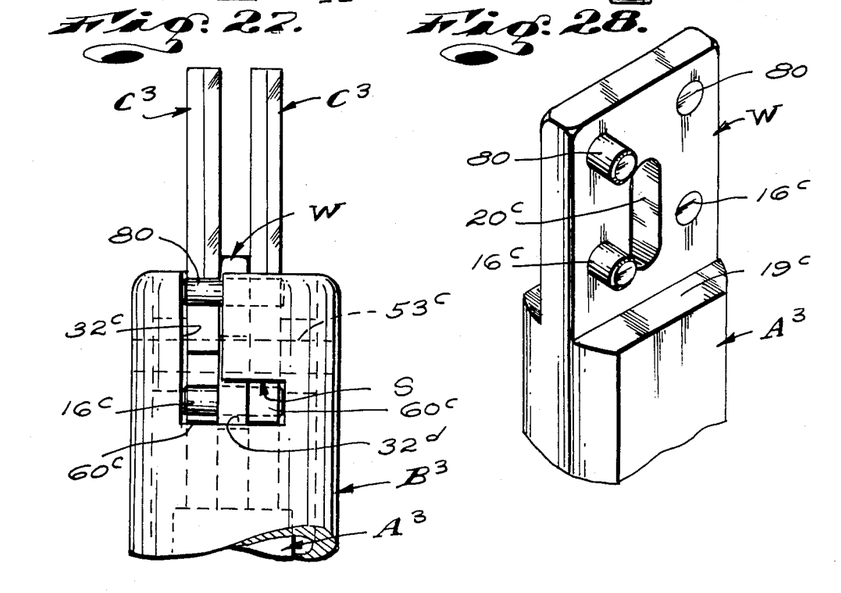
FIG. 27 is a view taken on line 27—27 on FIG. 23.
FIG. 28 is an isometric view of a part of the structure shown on FIGS. 23 through 27.

In FIGS. 23 through 28 of the drawings, I have shown another embodiment of my invention which is designed to facilitate making a device of titanium, which material is lightweight, extremely strong, and is stable in the environments in which my device is to be used. A principal shortcoming of titanium resides in the fact that it is so difficult to machine, form and otherwise work that it can only be used to establish simple, non-intricate parts. Accordingly, the embodiment of my invention now under consideration is designed to make the parts thereof of simple design and such that they can be advantageously made of titanium. Further, this embodiment of my invention is designed to enable the use of a single pivot pin 53-C for a pair of struts C-3. The pivot pin 53-C can be made considerably larger in diameter and therefore stronger than the pivot pins in the other embodiments of the my invention. Still further, the structure now under consideration is such that when the device is in its actuated or deplayed position, as shown in FIGS. 24 and 26 of the drawings, the ends of the lever arms 60-C on the struts C-3, which lever arms define the cam follower parts 61-C of the cam means M-3, establish latched engagement with stop edges S established in the sleeve B-3 of the device. With the lever arms of the struts latched with the sleeve, as noted, forces transmitted through the struts which tend to hyperactuate the struts and concentrate excessive forces onto the pivot pin 53-C are directed onto and between the sleeve B-3 and the shaft A-3.

The embodiment of my invention now under consideration is mechanically similar to the embodiment of the invention shown in FIGS. 15 through 17 of the drawings. The struts C-3 are slightly reproportioned and repositioned so that their pivotal axes are normal to and intersect the central longitudinal axis of the device and are engaged on and carried by related portions of the single pivot pin 53-C.

The sleeve B-3 is essentially the same as the sleeve in the form of the invention shown in FIGS. 15 through 17 except that the slots 32-C are made L-shaped and are characterized by or include circumferentially extending, radially opening extensions or returns 32-D at their lower ends. The returns 32-D establish downwardly disposed reaction edges or stops S to engage the lever arms 60-C of the struts. Also, the sleeve mounts and carries the single pivot pin 53-C as clearly shown.

The upper deployment end portion of the shaft A-3 is defined by a flat, vertical, central web W. The web W is on the central plane of the device which is normal to the axis of the pivot pin and has a vertical slot-like relief opening 20-C through which the pivot pin 53-C freely extends.

The web W is the counterpart of the stock of the shafts which occur between the recesses in the other embodiments of my invention and establish or define recesses in the shaft for the struts and lever arms.

The relief opening 20-C is the counterpart of the relieved portions 20 in the other embodiments of my invention and serve to accommodate and allow for free relative movement of the pivot pin relative to the shaft.

The shaft A-3 defines flat, upwardly disposed lower cam surfaces or parts 19-C adjacent the lower end of the web W. The lower cam surfaces engage the points and related edges of the cam followers defined by the lever arms on the struts.

The cam means M-3 are mechanically similar to the cam means in the embodiment of my invention shown in FIGS. 15 through of the drawings.

In the case illustrated, to simplify the structure and to facilitate its manufacture, the upper cam surfaces or cam parts 16-3 are simple, short, cam pins which are set in and project laterally from the web W.

As shown, stop pins 80, similar to the cam 16-C can be carried by the web to stop the struts in their unactuated positions, as clearly shown in the drawings. Finally, in this last embodiment of my invention, the outer or free end portion of the lever arms 60-C are extended or made longer so that when the struts are in their fully actuated or deployed position and the lower edges of the lever arms oppose and are stopped on the lower cam surfaces 19-C, the terminal end portions of the lever arms project radially outward from the shaft A-3 and into the extensions 32-D of the slots 32-C and establish stopped engagement with their related stops S in the sleeve, as clearly shown in FIGS. 24 and 26 of the drawings.

Referring to FIG. 24 of the drawings, it will be apparent that applied forces on the struts that tend to pivot them radially outward and downward beyond their fully actuated positions are conducted through the lever arms and directed onto and between the lower cam surfaces 19-C on the shaft A-3 and the stops S in the sleeve B-3. The effective distance between the force receiving portions of the lower cam surfaces 19-C and the stops S is great and affords substantial mechanical advantage to counter hyperactuation of the struts. The pivot pin is left substantially unbiased.

It is to be noted that in the use of implant devices of the character here concerned with, bone materials frequently grow in and about the devices and tend to foul and prevent operation of the devices from their fully actuated or deployed positions to their unactuated positions, preparatory to their being removed from within a bone structure. Accordingly, in carrying out my invention, considerable working clearances are established between certain parts and portions of the several embodiments of my invention to afford slop and/or play which is such that when the devices are moved from their actuated to their unactuated positions, bone material or the like that has collected or grown about and within the devices is readily and effectively displaced. Since the showing of such working clearances, slop and/or play would tend to obscure the mechanical aspects of the invention and are subject to substantial variations, no attempt has been made to show such clearances and the like.

Having described only typical preferred forms and embodiments of my invention, I do not wish to be limited to the specific details herein set forth but wish to reserve to myself any modifications and/or variations that might appear to those skilled in the art and which fall within the scope of the following claims.

Having described my invention, I claim:

1. An implant device for fixating bone portions in a living body comprising an elongate, vertical shaft defining the central axis of the device, said shaft has an upper deployment end portion and a lower securement end portion, said shaft has a plurality of circumferentially spaced elongate longitudinally extending radially outwardly opening strut accommodating recesses with upper and lower ends in its deployment end portion; first cam means parts on said shaft related to each recess; an elongate vertical sleeve with an upper deployment end portion and a lower securement end portion is engaged about and is shiftable axially relative to said shaft, said sleeve has circumferentially spaced longitudinally extending and radially opening strut accommodating slots, each registering with a related recess; first pivot means parts related to each slot at the upper end portion of said sleeve on a turning axis normal to and extending transverse the radial plane of the recess; a plurality of elongate flat blade-like struts with inner pivot ends and outer free ends, each strut is engaged in a related slot and recess with its flat plane parallel with said radial plane thereof; a second pivot means part at the pivot end of each strut and engaged with said first pivot means parts related to the slot in which the strut is engaged, said struts are pivotally movable relative to said sleeve between unactuated positions where they extend longitudinally within their related slots and recesses to actuated positions where they extend radially and axially outward from said slots and recesses; a lever arm projects from the pivot end of each strut and into its related recess; each lever arm has second cam means parts engaged with the first cam means parts in its related recess to pivot said arm between its unactuated and actuated positiions upon axial movement of said shaft relative to said sleeve; and manually accessible and operable drive means at and between said securement end portions of said shaft and sleeve to move said shaft axially relative to said sleeve.

2. The improved implant device set forth in claim 1 wherein said first cam means parts include a pair of axially spaced substantially upwardly and downwardly disposed cam surfaces in each recess; said second means parts define cam follower surfaces on the lever arm and positioned between and engaging the pair of cam surfaces in its related recess.

3. The improved implant device set forth in claim 1 wherein said second cam means parts related to each lever arm define substantially vertically spaced opposing cam surfaces on said lever arms, said first cam means parts related to each recess define came follower surfaces in driving engagement with and between the pair of cam surfaces of lever arm in the recess.

4. The improved implant device set forth in claim 1 wherein said first pivot means parts related to each slot includes a pair of pivot openings on an axis extending transverse the slots, said second pivot means part at the pivot end of each strut includes an elongate pivot pin in supporting engagement with said lever arm and having end portions supportingly engaged in a related pair of pivot openings.

5. The improved implant device set forth in claim 1 wherein said first pivot means parts related to each slot includes a pair of spaced pivot openings in the sleeve on an axis extending transverse the slot, said second pivot means parts related to the pivot end of each strut includes an elongate pivot pin carried by the strut and having end portions slidably engaged in its related pair of pivot openings, said first cam means related to each recess includes a pair of axially spaced substantially downwardly and upwardly disposed opposing cam surfaces in the slot; said second cam parts related to each lever arm define cam follower surfaces on the arm and engaging the pair of cam surfaces in its related recess.

6. The improved implant device set forth in claim 1 wherein said first pivot means parts related to each slot includes spaced pivot openings in the sleeve on an axis extending transverse the slot, said second pivot means part at the pivot end of each strut includes an elongate pivot pin carried by said lever arm on axes concentric with the axes of related pivot pin openings and with end portions slidably engaged in related pivot openings, said second cam parts on each lever arm include spaced opposing cam surfaces on said pivot arm projecting substantially radially from the turning axis of the strut, the first cam parts within each recess define cam follower surfaces in driving engagement with and between the cam surfaces of their related lever arms.

7. The improved implant device set forth in claim 1 wherein said drive means includes an elongate threaded drive part concentric with said central axis and drivingly connected with and between the deployment end portions of said shaft and sleeve and moving said shaft axially of said sleeve when rotated.

8. The improved implant device set forth in claim 1 wherein said drive means includes a manually engageable threaded drive part concentric with and positioned below the lower end of said shaft, an elongate coupling part depending from said shaft and threadedly engaged through said drive part and axially compressible spring means about said coupling part and in force transmitting engagement with and between said drive part and the deployment end portion of said sleeve.

9. The improved implant device set forth in claim 1 wherein said first pivot means parts related to each slot includes a pair of spaced pivot openings in the sleeve on an axis extending transverse said slot, said second pivot means part related to each strut includes an elongate pivot pin carried by the strut and having end portions slidably engaged in its related pair of pivot openings, said first cam means related to each recess include axially spaced substantially downwardly and upwardly disposed opposing cam surfaces and said second cam parts related to each lever arm define cam follower surfaces between and engaging a related pair of cam surfaces; said drive means includes an elongate threaded drive part concentric with said central axis and drivingly connected with and between the deployment end portions of said shaft and sleeve and moving said shaft axially of said sleeve when rotated.

10. The improved implant device set forth in claim 1 wherein said first pivot means parts related to each slot includes a pair of spaced pivot openings in the sleeve on an axis extending transverse the radial plane of the slot, said second pivot means part related to each strut includes a pivot pin carried by the strut and having end portions engaged in its related pair of pivot openings, said second cam parts on each lever arm include a pair of substantially vertically spaced opposing cam surfaces on the pivot arm, said first cam parts on the shaft and related to each recess define cam follower surfaces in the recess and in driving engagement with and between said cam surfaces on a related lever arm, said drive means includes an elongate threaded drive part concentric with said central axis and drivingly connected with and between the deployment end portions of said shaft and moving said shaft axially of said sleeve when rotated.

11. The implant device set forth in claim 1 wherein said flat blade-like struts have oppositely disposed longitudinally extending inner and outer edges, at least one of said edges is sharpened.

12. The implant device set forth in claim 1 wherein said flat blade-like struts have oppositely disposed longitudinally extending inner and outer edges, at least one of said edges is sharpened, said first cam means parts related to each recess include a pair of axially spaced substantially upwardly and downwardly disposed opposing cam surfaces; and said second cam means parts related to each lever arm define cam follower surfaces positioned between and engaged with a related pair of cam surfaces.

13. The implant device set forth in claim 1 wherein flat blade-like parts have oppositely disposed longitudinally extending inner and outer edges, said second cam means part on each lever arm defines vertically spaced opposing cam surfaces on the arm, said first cam means parts in each recess in the shaft define cam follower surfaces in driving engagement with and between the cam surfaces of related lever arms.

14. The implant device set forth in claim 1 wherein said elongate flat blade-like struts have flat oppositely disposed sides on planes normal to the turning axes of said struts and have oppositely disposed longitudinally extending inner and outer edges, at least one of said edges is sharpened, said slots slidably receive and support said struts, said first pivot means parts include a pair of axially spaced pivot openings in the sleeve adjacent each on an axis normal to and extending transverse the radial planes of the slot, said second pivot means part related to each strut includes an elongate pivot pin carried by said lever arm and having end portions engaged in a related pair of pivot openings, said first cam means parts include a pair of axially spaced substantially downwardly and upwardly disposed opposing cam surfaces in each recess; and said second cam means parts on each lever arm define cam follower surfaces on the lever arm and positioned between and engaging a related pair of cam surfaces.

15. The implant device set forth in claim 1 wherein said elongate flat blade-like struts have flat oppositely disposed sides on planes normal to the turning axes of said struts and have oppositely disposed longitudinally extending inner and outer edges, at least one of said edges is sharpened, said slots slidably engage the side of and support said struts, said first pivot means parts related to each slot include a pair of axially spaced pivot openings in the sleeve on an axis normal to and extending transverse the radial planes of the slot, said second pivot means part related to each strut includes an elongate pivot pin carried by the lever arm and having end portions slidably engaged in a related pair of pivot openings, said second cam parts on the lever arms define substantially vertically spaced cam opposing surfaces on the lever arms, said first cam parts in each recess in the shaft define cam follower surfaces in driving engagement with and between the pair of cam surfaces on the lever arm related thereto.

16. The implant device set forth in claim 1 wherein said elongate flat blade-like struts have oppositely disposed sides on planes normal to the turning axes of said struts and have oppositely disposed longitudinally extending inner and outer edges, at least one of said edges is sharpened, said slots slidably engage said side of and support said struts, said first pivot means parts include a pair of axially spaced pivot openings in the sleeve adjacent each slot on an axis extending transverse the radial planes of the slot, said second pivot means part related to each strut includes an elongate pivot pin carried by the strut and having end portions slidably engaged in the pair of pivot openings related to it, said first cam means in each recess in the shaft include a pair of axially spaced substantially downwardly and upwardly disposed opposed cam surfaces; said second cam parts on the lever arms define cam follower surfaces on the pivot arm and engaged between the pair of cam surfaces in the recess related to the lever arm, said drive means includes an elongate threaded drive part concentric with said central axis and drivingly connected with and between the deployment end portions of said shaft and sleeve and moving said shaft axially of said sleeve when rotated.

17. The implant device set forth in claim 1 wherein said elongate flat blade-like struts have oppositely disposed sides on planes normal to the turning axes of said struts and have oppositely disposed longitudinally extending inner and outer edges, at least one of said edges is sharpened, said slots slidably accommodate and support said struts, said first pivot means parts related to each slot in the sleeve include a pair of axially spaced pivot openings in the sleeve on an axis extending transverse the radial planes of the slot, said second pivot means part on each lever arm includes an elongate pivot pin supportingly engaged with the lever arms and having end portions supportingly engaged in the pair of pivot openings in the sleeve related to it, said second cam parts on each lever arm define spaced vertically spaced cam surfaces projecting radially from said turning axes of their related strut, said first cam parts related to each recess in the shaft define cam follower surfaces in driving engagement with and between the pair of cam surfaces on their related lever arm, said drive means includes an elongate threaded drive part concentric with said central axis and drivingly connected with and between the deployment end portions of said shaft and sleeve and moving said shaft axially of said sleeve when rotated.

18. The improved implant device set forth in claim 1 wherein said first pivot means parts related to each slot include a pair of axially spaced pivot openings in the sleeve on an axis extending transverse the radial planes of the slot, said second pivot means part on each lever arm includes an elongate pivot pin supporting the lever arm on an axis concentric with the axis of and having end portions engaged in a related pair of pivot openings; and releasing means to disconnect said struts from said sleeve including enlarged access openings in said sleeve between the ends of and intersected by said slots, a manually operable releasing tool including a body slidably engaged about the securement end portion of said sleeve and shiftable axially relative thereto, axially upwardly projecting resilient arms on said body aligned with and positioned outward of said slots, inwardly projecting wedges on said arms releasably engageable in said access openings and shiftable upwardly into said slots to spread apart the upper portions of said sleeve defining said slots and move the pivot openings from engagement with said pivot pins.

* * * * *